United States Patent [19]

Burton

[11] Patent Number: 4,526,918

[45] Date of Patent: Jul. 2, 1985

[54] PHENOLIC PHOSPHITE ANTIOXIDANT AND PROCESS FOR PREPARATION THEREOF

[75] Inventor: Lester P. J. Burton, Pleasant Ridge, Mich.

[73] Assignee: Ethyl Corporation, Richmond, Va.

[21] Appl. No.: 350,085

[22] Filed: Feb. 18, 1982

[51] Int. Cl.$^3$ .................. C08K 5/52; C07F 9/146; C07F 9/145

[52] U.S. Cl. .................. 524/150; 524/128; 524/152; 524/342; 260/930; 260/953; 260/973; 260/976

[58] Field of Search .............. 524/128, 150, 152, 342; 260/930, 973, 976, 953

[56] References Cited

U.S. PATENT DOCUMENTS

| | | |
|---|---|---|
| 3,026,264 | 3/1962 | Rocklin et al. .................. 524/342 |
| 3,039,993 | 6/1962 | Friedman .................. 260/45.8 |
| 3,567,863 | 3/1971 | Spacht .................. 524/152 |
| 3,949,024 | 6/1976 | Beck et al. .................. 260/953 |
| 4,187,212 | 2/1980 | Zinke et al. .................. 260/45.8 NT |
| 4,233,207 | 11/1980 | Spivack .................. 260/45.7 |
| 4,246,170 | 1/1981 | Evans .................. 524/128 |
| 4,257,927 | 3/1981 | Leistner et al. .................. 524/128 |
| 4,282,141 | 8/1981 | Minagawa et al. .................. 260/45.7 |

Primary Examiner—Veronica P. Hoke
Attorney, Agent, or Firm—Donald L. Johnson; John F. Sieberth; John F. Hunt

[57] ABSTRACT

A phenolic phosphite antioxidant for use alone in polyolefins or in admixture with synergists, phenolic/phosphite antioxidants, and the like. The adduct formed by reacting a phosphorus trihalide, preferably $PCl_3$, with 1,3,5-trimethyl-2,4,6-tris(3,5-di-tert-butyl-4-hydroxybenzyl)benzene is useful for antioxidant activity in organic materials.

24 Claims, No Drawings

PHENOLIC PHOSPHITE ANTIOXIDANT AND PROCESS FOR PREPARATION THEREOF

BACKGROUND OF THE INVENTION

I. Field of the Invention

This invention relates in general to antioxidants, and antioxidant synergists for organic materials and in particular to a process for making a phenolic phosphite by reacting a phosphorus trihalide, e.g., PCl₃ and 1,3,5-trimethyl-2,4,6-tris(3,5-di-tert-butyl-4-hydroxybenzyl)-benzene as well as the adducts made thereby.

II. Description of the Prior Art

Phosphites are used in organic polymers and other organic substrates as high temperature antioxidants. The phosphites are generally considered better than phenolic antioxidants at high temperatures because they eliminate hydroperoxides which decompose and lead to autooxidation chain reactions. Thus phosphites are important for hydrolytic stability during polyolefin extrusion and during other operations with organic substrates.

Various phophites are well known in the art such as the aryl phosphite shown in U.S. Pat. No. 4,282,141 to Minagawa et al, and the phenyl phosphonites disclosed in U.S. Pat. No. 4,233,207 to Spivack.

Phenolic and phosphite antioxidants are often used together in polyolefin homopolymers and copolymers to provide antioxidant protection for both low and high temperature exposure. Unfortunately additional expense is encountered as more additives in larger amounts are needed for a polymer. Thus there exists a need for effective antioxidants at a reasonable additive price, not only for polyolefins but other substrates as well.

Other phosphite antioxidants are those disclosed in U.S. Pat. No. 4,187,212 to Zinke et al, and U.S. Pat. No. 3,039,993 to Friedman.

Various alkylated phenolics are well known in the art such as those disclosed in U.S. Pat. No. 3,026,264. The high temperatures referred to above with regard to phosphites, are high enough to affect the rigidity of a polyolefin, but are generally below the point where the polyolefin would immediately decompose or ignite.

SUMMARY OF THE INVENTION

According to the present invention, a phosphorus trihalide is reacted with 1,3,5-trimethyl-2,4,6-tris(3,5-di-tert-butyl-4-hydroxybenzyl)benzene to form an adduct. The adduct is known to have about five major components. The adduct is also known to have about 0.1 to 9.0 weight percent phosphorus and about 0.0 to 5.0 weight percent chlorine. Thus the invention is a process for making the adduct, the adduct per se, compositions including the adduct, and methods of using the adduct to protect an organic material.

The process for making the adduct comprises reacting a phophorus trihalide such as PCl₃, PF₃, or PBr₃ with the substituted tris benzene compound I:

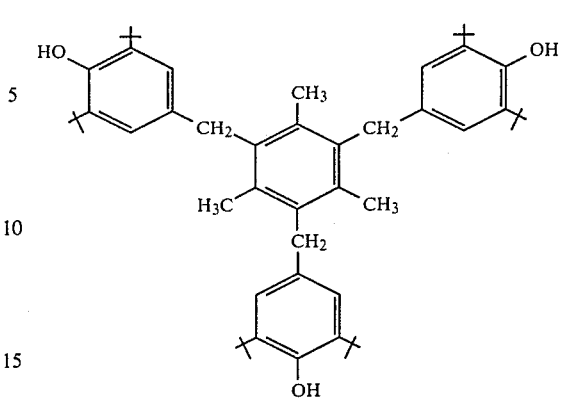

The reaction is preferably carried out by heating about 0.1 to 2.0 mole parts phosphorus trihalide with each mole part of the phenolic compound I. The compound I is available from Ethyl Corporation as Ethanox ® 330 phenolic antioxidant. Reaction temperatures suitable for the reaction fall within the range of 20° to 70° C. at normal pressure but this range may vary somewhat for subatmospheric or superatmospheric reaction pressures or higher boiling solvents which are also suitable for the reaction.

The most preferred phosphorus trihalide for making the novel adduct is PCl₃ since the adduct made with PCl₃ has shown not only superior antioxidant activity but synergistic activity as well.

The adduct made by the process of this invention protects substrate polyolefins, for example, in a manner previously achieved only by the addition of both a phenolic antioxidant and a phosphite compound. Moreover, the protection is in some cases superior to such combination-protected polyolefins.

The adduct of the present invention is known to contain at least one component (of several) which has at least one P-O bond. Thus the phosphorus from PX₃ is likely linked to the compound I structure at the oxygen atom from one of the three available hydroxy groups. The adduct of the invention combines the advantages of both a phenolic and a phosphite antioxidant.

Furthermore, the adduct formed by the process of the invention has shown synergy with other antioxidants in polyolefins. Another useful synergist for the adduct of the invention is distearyl thiodipropionate (DSTDP).

Also according to the present invention, stabilized organic compositions are provided which contain an antioxidant amount of the novel adduct. The adduct contains components which are new compounds.

The invention is, therefore, a process for making a phenolic phosphite adduct, said process comprising reacting a phosphorus trihalide with 1,3,5-trimethyl-2,4,6-tris(3,5-di-tert-butyl-4-hydroxybenzyl)benzene to form an adduct of the two reactants.

The invention also includes the isolated adduct of the above reaction.

The invention also includes organic material normally susceptible to gradual oxidative degradation, containing an antioxidant amount of the adduct formed by reacting a phosphorus trihalide with 1,3,5-trimethyl-2,4,6-tris(3,5-di-tert-butyl-4-hydroxybenzyl)benzene.

The invention also includes a method for protecting an organic material normally susceptible to gradual degradation in the presence of oxygen, said method comprising adding to said polyolefin an antioxidant amount of the adduct formed by reacting a phosphorus trihalide with 1,3,5-trimethyl- 2,4,6-tris(3,5-di-tert-butyl-4-hydroxybenzyl)benzene.

Finally, the invention also includes compositions of the adduct of reaction in combination with a specific polyolefin, an antioxidant, or both.

It is therefore an object of the invention to provide a process for making an adduct of compound I and a phosphorus trihalide.

It is also an object of the present invention to provide an adduct which shows synergism with other phenolic and/or phosphite antioxidants.

It is also an object of the invention to protect a polyolefin with the adduct of a phosphorus trihalide and compound I, either alone or with another additive.

These and other objects of the present invention will be better understood by a reading of the following detailed description.

DESCRIPTION OF THE PREFERRED EMBODIMENTS

A preferred embodiment of the invention is a reaction of a phosphorus trihalide with compound I. A preferred embodiment is also a composition of organic material and an antioxidant portion of the adduct of the invention.

According to a preferred embodiment of the invention, the compound I is reacted with a phosphorus trihalide by heating for an extensive time such as 24 hours. It is noted that the adduct appears to be formed in a much shorter time (less than one hour) but the heating may be continued for thoroughness.

The $PX_3$ and compound I are preferably reacted by first forming an alkali metal salt such as the sodium salt of compound I in a solvent before refluxing with $PX_3$. Preferably the $PX_3$ is also dissolved in a small portion of the same or a compatible solvent. Also the reaction mixture may be cooled, washed with alcohol, and chemically dried to improve color characteristics.

It is contemplated that the adduct of $PX_3$ and phenolic compound I will most advantageously be used with a thioester, but may be used alone. It may also be more beneficial in certain polyolefin or other organic substrates and for certain purposes to use the adduct in admixture with a phenolic antioxidant, whether pre-blended or separately incorporated into an organic substrate.

The antioxidant adduct of the present invention can be used in a broad range of organic material normally subject to gradual degradation in the presence of oxygen during use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not flame retarding additives nor flame suppressing additives and the degradation protected against is not combustion but rather, the gradual deterioration of the organic composition due to the effects of oxygen over an extended period of time.

The adduct of the present invention contains components incorporating the structure of compound I and should be usable with the broad array of organic materials for which compound I is used. Those organic materials include plastics, resins, rubber, and waxes. The adduct of the invention is a highly effective, odorless stabilizer with exceptionally low volatility.

Examples of organic materials in which the additives may be useful include polymers, both homopolymers and copolymers, of olefinically unsaturated monomers, for example, polyolefins such as polyethylene, polypropylene, polybutadiene, polybutylene, low density polyethylene, linear low density polyethylene (often made from the primary monomer ethylene and about 5–10% comonomer) and the like.

Also, poly-halohydrocarbons such as polyvinyl chloride, polychloroprene, polyvinylidene choride, polyfluoro olefins, and the like may be afforded stabilization. The additives may be used to provide antioxidant protection in natural and synthetic rubbers such as copolymers of olefinically unsaturated monomers including styrene-butadiene rubber (SBR rubber), ethylene-propylene copolymers, ethylene-propylenediene terpolymers such as the terpolymer of ethylene, propylene and cyclopentadiene or 1,4-polybutadiene rubber may be protected. Poly-2-chloro-1,3-butadiene (neoprene) and poly-2-methyl-1,3-butadiene (isoprene rubber) may be stabilized by the present additives. Likewise, acrylonitrile-butadiene-styrene (ABS) resins are effectively stabilized. Ethylenevinyl acetate copolymers may be protected, as may be butene-methylacrylate copolymers. Nitrogen-containing polymers such as polyurethanes, nitrile rubber, and lauryl acrylate-vinyl-pyrrolidone copolymers may be effectively stabilized. Adhesive compositions such as solutions of polychloroprene (neoprene) in toluene may be protected.

Petroleum oils such as solvent-refined, hydrocracked, midcontinent lubricating oil and Gulfcoast lubricating oils may be effectively stabilized. In hydrocarbon lubricating oils, both mineral and synthetic, the present additives may be particularly effective when used in combination with a zinc dihydrocarbyldithiophosphate, e.g. zinc dialkyldithiophosphate or zinc dialkaryldithiophosphate.

Synthetic ester lubricants such as those used in turbines and turbojet engines may be given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate may be effectively protected. Heavy petroleum fractions such as tar and asphalt may also be protected should the need arise.

Polyamides such as adipic acid-1,6-diaminohexane condensates and poly-6-aminohexanoic acid (nylon) may be effectively stabilized. Polyalkylene oxides such as copolymers of phenol with ethylene oxide or propylene oxide may be stabilized. Polyphenyl ethers such as poly-2,6-dimethylphenyl ether formed by polymerization of 2,6-dimethylphenol using a copper-pyridine catalyst may be stabilized. Polycarbonate plastics and other polyformaldehydes may also be protected.

Linear polyesters such as phthalic anhydride-glycol condensates may be given a high degree of protection.

Other polyesters such as trimellitic acid-glycerol condensates may also be protected. Polyacrylates such as polymethylacrylate and polymethylmethacrylate may be effectively stablilized. Polyacrylonitriles and copolymers of acrylonitriles with other olefinically unsaturated monomers such as methylmethacrylates may also be effectively stabilized.

The adduct of the invention may be used to protect any of the many organic substrates to which an antioxidant is normally added. It can be used where economics permit to protect such substrates as asphalt, paper, fluorocarbons such as teflon, polyvinyl acetate, polyvinylidene chloride, coumarone-indene resins, polyvinyl ethers, polyvinylidene bromide, polyvinyl bromide, acrylonitrile, vinyl bromide copolymer, vinyl butyral resins, silicones such as dimethyl-silicone lubricants, phosphate lubricants such as tricresylphosphate, and the like.

The adduct may be incorporated into the organic substrate in a small but effective amount so as to provide the required antioxidant protection. A useful range is from about 0.01 to about 0.5 weight percent, and a preferred range is from about 0.05 to 0.3 weight percent.

Methods of incorporating the adduct into the substrate are well known. For example, if the substrate is liquid the adduct can be merely mixed into the substrate. Frequently the organic substrate is in solution and the adduct is added to the solution and the solvent removed. Solid organic substrates can be merely sprayed with a solution of the adduct in a volatile solvent. For example, stabilized grain products might be made by spraying the grain with a toluene solution of the adduct. In the case of rubbery polymers the adduct may be added following the polymerization stage by mixing it with the final emulsion or solution polymerization mixture and then coagulating or removing solvent to recover the stabilized polymer. It can also be added at the compounding stage by merely mixing the adduct with the rubbery polymer in commercial mixing equipment such as a Banbury blended. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

The following examples serve to explain the invention in the best mode now known to me.

EXAMPLE 1

The adduct of the invention was prepared in two steps, first forming the sodium salt of 1,3,5-trimethyl-2,4,6-tris(3,5-di-tert-butyl-4-hydroxybenzyl)benzene (compound I) and then reacting phosphorus trichloride with the heated sodium salt of compound I.

Tetrahydrofuran (THF, 50 ml) was dried over Na/benzophenone. A 0.021 mole (0.52 g) portion of 98 percent NaH and a 0.02 mole (15.5 g) portion of compound I were cautiously combined with the THF in a round bottom flask equipped with a stirrer and addition funnel. The mixture effervesced briefly and formed a slurry which was brought to reflux for one hour.

A solution of 0.07 mole (0.6 ml) PCl$_3$ in 10 ml dry THF was added dropwise to the refluxing slurry and then allowed to reflux for 22 hours (although reaction appeared complete in only a short period). The reaction mixture was cooled, poured over 150 ml ethylacetate to hold the organics, then washed twice with a total of 200 ml 50% saturated NaCl aqueous solution to remove aqueous solubles including NaCl, and finally dried over anhydrous Na$_2$SO$_4$ after removing the aqueous layer in a separating funnel. A pale yellow solid (16.7 g) with a melting point of 130°–140° C. was recovered. The acid number of the product both before and after boiling in water for 20 minutes was 0.0.

Further analyses showed the presence of five major components one of which appeared as compound I in a thin layer chromatography comparison. About 51% compound I remained in the adduct. The adduct contained 0.93 weight percent phosphorus and 1.77 weight percent chlorine. Washing the adduct with ethanol yields a white solid with only 1.5 weight percent phosphorus. Both the initially produced yellow adduct and the ethanol-washed white product were subsequently used in a polyolefin or other organic material.

With the amount of chlorine present in the adduct of Example 1 it was unexpected that the adduct would display antioxidant activity since most commercial antioxidants require lower chlorine concentrations. On the other hand, most commercial antioxidants have a high amount of phosphorus. For example compare distearyl pentaerythritol diphosphite at 7.2–7.8 weight percent phosphorus. Nevertheless, good results have been realized.

EXAMPLE 2

The initial yellow adduct made in Example 1 (before ethanol wash), 0.02 g and about 0.05 g distearyl thiodipropionate (DSTDP) were dissolved in a few drops of methylene chloride and mixed in a blender. The solution was poured into about 20 g Norchem's Profax-6500 (TM) polypropylene (in powder form). Thereafter the stabilized polypropylene was compression molded at 400° F. in a Pasadena Hydraulic Press into several one inch by ½ inch plaques of about 2,5 mils thickness. The plaques were thereafter placed in an air circulating oven set at 150° C. and periodically checked for cracks or other signs of degradation caused by the oven aging.

EXAMPLES 3-4

Other plaques were similarly prepared so as to provide polypropylene with about 0.1 and 0.3 weight percent compound I only (without DSTDP). For comparison, an unprotected polypropylene plaque develops cracks and completely degrades within about four hours. Polypropylene protected with 1,3,5-trimethyl-2,4,6-tris(3,5-di-tert-butyl-4-hydroxybenzyl)benzene (compound I) alone at about 0.3 weight percent fails at about 600 hours. Polypropylene protected with a small portion of compound I plus a phosphite antioxidant such as distearyl thiodipropionate (DSTDP) fails at about 1008 hours.

EXAMPLE 5

Several plaques were prepared from the alcohol-washed white adduct of Example 1 in precisely the same manner and consistency as Example 2.

The oven aging results for Examples 2–5 are summarized in the table below:

TABLE

| | 150° C. Polypropylene Oven Aging | | |
|---|---|---|---|
| | Wt. % | | |
| Ex. No. | Adduct | DSTDP | Hours to Fail |
| 2 | 0.10 | 0.25 | 2712 |
| 3 | 0.10 | — | 936 |
| 4 | 0.30 | — | 2064 |
| 5 | 0.10 | 0.25 | 1752 |
| Compound I alone at 0.3% | | | 600 |
| Compound I at 0.10% plus 0.25% DSTDP | | | 1008 |

Thus the adduct of the invention performed better at 0.1 weight percent (Example 3) than did phenolic antioxidant compound I at about 0.3 weight percent. Also the results of Example 2 shows the unexpected synergistic improvment of the adduct with a thioester, DSTDP over a phenolic antioxidant plus DSTDP.

It is possible to vary the organic substrate of the invention, the method of incorporating the adduct and/or some other features of the invention without departing from the scope or spirit thereof as defined by the appended claims.

I claim:

1. A process for making a phenolic phosphite adduct, said process comprising reacting at least about 0.05 mole parts of a phosphorus trihalide of formula $PX_3$ where the X are halides with one mole part 1,3,5-trimethyl-2,4,6-tris(3,5-di-tert-butyl-4-hydroxybenzyl) benzene to form a reaction product mixture including at least one adduct of the two reactants.
2. The process of claim 1 wherein the phosphorus trihalide is $PCl_3$.
3. The process of claim 1 wherein the reactants are heated at about reflux temperature.
4. The process of claim 2 wherein the reactants are heated at about reflux temperature for about one hour.
5. An isolated adduct formed by the process of claim 1.
6. The process of claim 1 wherein said adduct is prepared by forming an alkali metal salt of 1,3,5-trimethyl-2,4,6-tris(3,5-di-tert-butyl-4-hydroxybenzyl)benzene and then heating a phosphorus trihalide therewith.
7. The process of claim 6 wherein said alkali metal is sodium provided from NaH.
8. The process of claim 6 wherein the process is carried out in an organic solvent.
9. The process of claim 8 wherein the organic solvent is tetrahydrofuran (THF).
10. An isolated adduct formed by the process of claim 2.
11. The reaction product mixture of claim 1 wherein said mixture contains five major components, at least one of said components being an adduct of the reactants and having at least one P-O bond.
12. The reaction product mixture of claim 1 wherein said mixture is characterized by a phosphorus content of about 0.1 to 9.0 weight percent and a chlorine content of about 0.0 to 5.0 weight percent.
13. The adduct of claim 5 in combination with 1,3,5-trimethyl-2,4,6-tris(3,5-di-tert-butyl-4-hydroxybenzyl)benzene.
14. Organic material normally susceptible to gradual oxidative degradation, containing an antioxidant amount of an adduct formed by reacting at least about 0.05 mole parts of a phosphorus trihalide of formula $PX_3$ where the X are halides with one mole part 1,3,5-trimethyl-2,4,6-tris(3,5-di-tert-butyl-4-hydroxybenzyl)benzene.
15. The combination of claim 14 wherein said organic material is a polyolefin.
16. The combination of claim 15 wherein said polyolefin is selected from polybutylene, polypropylene, polyethylene, low density polyethylene, and linear low density polyethylene.
17. The combination of claim 14 wherein said adduct is present in an antioxidant amount of about 0.05 to 0.30 weight parts per 100 weight parts organic material.
18. The combination of claim 14 and further comprising an additional synergist, phosphite, or phenolic antioxidant.
19. A method for protecting an organic material normally susceptible to gradual degradation in the presence of oxygen, said method comprising adding to said organic material an antioxidant amount of an adduct formed by reacting at least about 0.05 mole parts of a phosphorus trihalide of formula $PX_3$ where the X are halides with one mole part 1,3,5-trimethyl-2,4,6-tris (3,5-di-tert-butyl-4-hydroxybenzyl)benzene.
20. The method of claim 19 wherein said organic material is a polyolefin.
21. The method of claim 20 wherein said polyolefin is selected from polypropylene, polybutylene, polyethylene, low density polyethylene, and linear low density polyethylene.
22. The method of claim 21 wherein said polyolefin is polypropylene.
23. The method of claim 19 wherein said antioxidant amount added is at least about 0.05 parts by weight adduct per 100 parts by weight organic material.
24. The method of claim 19 wherein said trihalide is $PCl_3$.

* * * * *

UNITED STATES PATENT AND TRADEMARK OFFICE
CERTIFICATE OF CORRECTION

PATENT NO. : 4,526,918

DATED : JULY 2, 1985

INVENTOR(S) : LESTER P. J. BURTON

It is certified that error appears in the above-identified patent and that said Letters Patent is hereby corrected as shown below:

On the title page;

The reference cited in the patent reads "3,567,863" and the correct patent number should be -- 3,567,683 --.

Column 1, line 27, reads "phophites" and should read -- phosphites --.

Column 1, line 67, reads "phophorus" and should read -- phosphorus --.

Column 6, line 42, reads "2,5" and should read -- 2.5 --.

Signed and Sealed this

Fifteenth Day of October 1985

[SEAL]

Attest:

Attesting Officer

DONALD J. QUIGG

Commissioner of Patents and Trademarks—Designate